United States Patent [19]
Nayak

[11] Patent Number: 5,989,535
[45] Date of Patent: Nov. 23, 1999

[54] POLYMERIC BIOADHESIVE EMULSIONS AND SUSPENSIONS AND METHODS OF TREATMENT

[75] Inventor: Smita Nayak, Marlton, N.J.

[73] Assignee: Soma Technologies, Morganville, N.J.

[21] Appl. No.: 08/914,338

[22] Filed: Aug. 15, 1997

[51] Int. Cl.$^6$ .............................. A61K 47/32; A61K 9/02
[52] U.S. Cl. .................................... 424/78.02; 424/78.18; 424/78.29; 424/430; 424/433; 424/434; 424/435; 424/436
[58] Field of Search ............................. 424/78.02, 78.03, 424/78.18, 78.29

[56] References Cited

U.S. PATENT DOCUMENTS

| | | | |
|---|---|---|---|
| 5,194,253 | 3/1993 | Garrido | 424/78.03 |
| 5,437,867 | 8/1995 | Vichroski et al. | 424/78.02 |
| 5,508,029 | 4/1996 | Petchul et al. | 424/78.03 |
| 5,573,768 | 11/1996 | Afriat et al. | 424/78.02 |
| 5,635,171 | 6/1997 | Nadaud | 424/78.02 |

*Primary Examiner*—Peter F. Kulkosky

[57] ABSTRACT

Bioadhesive/mucoadhesive composition in a suspension or emulsion form that delivers drugs to the target tissue in a sustained manner is formulated. A composition, method of manufacture and its application in treatment of mammalian tissue are disclosed. The composition includes a bioadhesive/mucoadhesive polymer in an emulsion or suspension form along with a treating agent. The treating agent could be as simple as water as in the case of mucoadhesive moisturizing agent. The bioadhesive/mucoadhesive polymer is a water dispersible high molecular weight crosslinked polyacrylic acid copolymer with free carboxylic acid groups further crosslinked with a combination mono, di and polyvalent metal ions, cationic polymers and surfactants. Type of metal ion and their concentration can be adjusted to get the desired bio/mucoadhesive properties along with several physical properties that are important to the formulation of dosage forms. The viscosity of the formulation can be reduced substantially by crosslinking with metal ions or by incorporating anions or cations in 0.01 to 5% to get low viscosity product with higher polymer concentration, which is important in several dosage forms. The concentration of the polymer ranges from 0.05 to 20.0 percent depending on the crosslinking and the viscosity of the product.

18 Claims, No Drawings

POLYMERIC BIOADHESIVE EMULSIONS AND SUSPENSIONS AND METHODS OF TREATMENT

TECHNICAL FIELD

This invention relates to formulation and manufacture of bio/mucoadhesive drug delivery systems. These formulations are intended for the targeting of skin, oral cavity, rectal mucous membrane, gastric mucosa, intestinal mucosa, nasal passage and vaginal tissue.

BACKGROUND ART

Several bioadhesive drug delivery systems based on a variety of polymers have been described in patents and in literature. Majority of these patents concentrate on the adhesion of the drug to the gastric mucosa in order to retain the drug for a prolonged period of time in the target area. Such formulations tend to be solid products to be hydrated at the site of action for proper attachment to the tissue. Several polymers hydrate in presence of water and hydrophilic solvents and adhere to biological surfaces. These polymers alone or in combination with others polymers and active ingredients have been formulated for use in several commercial products. The first such commercial product based on a combination of gelatin, pectin and sodium carboxymethylcellulose in a hydrocarbon gel vehicle was marketed under the trademark Orabase® by Hoyt Laboratories, a division of Colgate-Palmolive Co. Similar product based on polyacrylic acid based polymer in water is marketed under the trademark Replens® by Warner-Lambert Co.

A composition containing 50 to 90 percent of cellulose ether and 5 to 50 percent homo or copolymer of acrylic acid is described in U.S. Pat. No. 4,226,848 as bioadhesive preparation for oral and nasal cavities. Acrylic polymer described in this patent is a lightly crosslinked acrylic acid allyl sucrose copolymer available under the trademark Carbopol®934 from B. F. Goodrich Chemical Co. Polyacrylic acids and their salts are also described in U.S. Pat. No. 4,226,484 at a concentration of 0.2 percent by weight as water-soluble polymers with desired viscosity.

Polyacrylic acid crosslinkced with divinylglycol commercially known as Polycarbophil is described in U.S. Pat. No. 5,225,196 as a bioadhesive polymer suitable for sustained release of medicaments. Bioadhesive water soluble copolymer of glycerol and methacrylic acid commonly known as polyglycerol methacrylate is described in U.S. Pat. No. 4,863,725.

BRIEF DESCRIPTION OF THE INVENTION

This invention describes bio/mucoadhesive compositions that contain crosslinked carboxy-functional polymer which is water—swellable and water soluble that can be made water insoluble by one or more of the following chemical or physical interactions:

a) chemical interaction with mono, di or poly valent cations to reduce the solubility b) chemical interaction with a combination of mono, di and polyvalent ions to reduce solubility c) Physical interaction between mono, di and trivalent anions to reduce solubility d) Chemical interaction with amino functional organic compounds to reduce solubility d) physical and chemical interaction between two different polymer strands to produce large insoluble molecule e) Utilize combinations of all of the above.

The finely divided crosslinked carboxy-functional copolymer is dispersed in a hydrophobic medium to get a pourable consistency which is then added to an aqueous solution containing the said ingredients that modify the properties of the major polymer to get an oil in water emulsion, latex or suspension. Traditionally, these type of polymers are very difficult to distribute in hydrophilic medium in large quantity due to the high viscosity of the dispersions. Viscosity is the limiting factor in incorporation of hydrophilic polymers in hydrophilic medium. Concentration of the polymer will dictate the outcome of sustained release or bioadhesion to the target site. In majority of the cases it is impossible to disperse even two percent polymer in aqueous systems without any lump formations. High-energy input is required in this type of system to incorporate even small amount of polymers. This invention overcomes problems associated in incorporation of large amount of polymer in the hydrophilic systems even to the extent of 10 to 20 percent with substantial reduction in the viscosity of the final product so that the resulting formulation has usable range of viscosity for therapeutic use. The final products prepared from this invention have better consumer acceptance due to the superior physical characteristics compared to the marketed products. These types of compositions can be used to administer drugs systemically or locally in sustained or immediate release dosage forms. Compositions of the invention can be formulated as liquids, creams, gels, suspensions, emulsions, soft gelatin capsules, hard gelatin capsules and hard-boiled candy with center fills.

DETAILED DESCRIPTION OF THE INVENTION

The present invention relates to polymeric controlled release composition specifically targeted to the organs that contain mucus membranes at the interface. The polymeric resin component of this invention comprises at least twenty five percent by weight of the resin as carboxylic acid groups with pKa of approximately 6.0±0.5. The carboxy polymer could be linear polyacrylic acid resin or crosslinked resins with average molecular weight between 2,00,000 to 7,00,000 for linear polymers and could run into several billions for crosslinked polymers. The polymer could be derived from carboxylic acid containing monomers like acrylic, alkyl acrylate, lactic, maleic, itaconic and citraconic acids and their combinations. Crosslinking agent could be polyalkenyl polyethers like allyl sucrose, allyl pentaerythritol and divinylgylcol in 0.05 to 2.0 percent. Pharmaceutically acceptable resins available under brand name of Carbopol, Noveon and Pemulen resins (from B.F. Goodrich co., Specialty Polymers and Chemical Division, Cleveland, Ohio U.S.A.) are useful in this invention. Crosslinked polymers polymerized in non-benzene solvent are preferred due to the carcinogenic potential of residual benzene.

Polyacrylic acid resins hydrate in water to form viscous solution or suspension depending on their concentration. Viscosity of the polymer solution or suspension also depends on the extent of neutralization of the free carboxylic acid groups by different type of cations. Monovalent cations tend to increase viscosity several fold whereas di and polyvalent cations tend to decrease the viscosity of the hydrated polymers. Increased neutralization of the carboxylic acid group by divalent and polyvalent cations will result in precipitation of the polymer from the solution. Mono, di and polyvalent anions have dramatic effect on the viscosity of lightly crosslinked polyacrylic acid polymers. Chloride, sulphate, nitrate and phosphate are some of the important biologically accepted anions that can be used. Sodium chloride is a good example, which can effectively reduce the viscosity of the polymeric dispersions and in turn can increase the amount that can be incorporated into the product without reducing the adhesive power. The viscosity of the final product can be controlled by balancing several factors: controlling the crosslinking of the polymer by di and polyvalent cations, neutralization of the carboxylic acid groups of the polymer with monovalent cations and controlling concentration of mono and poly valent anions. Most preferred mono valent cations are potassium and sodium and the most preferred divalent cation is zinc. Zinc has high affinity for the sulfhydral group that is part of several biological proteinacious surfaces.

Basic polyamines like dimethylaminoethyl methacrylate and cationic surfactants like cetylpyridinium chloride can be utilized to neutralize or crosslink the copolymer. Neutralization of the lightly crosslinked polymer dispersed in water with cetylpyridinium chloride results in precipitation of the polymer from the aqueous solutions. Such precipitates exhibit strong bioadhesive properties on biological surfaces. This is particularly useful in controlled release bioadhesive antimicrobial preparations intended for use on mucous membrane. Cetylpyridinium chloride and zinc can be effectively delivered to the oral mucosa by this controlled crosslinking and neutralization of the polyacrylic acid copolymer. The rate of addition and the final concentration of the crosslinking agents can effectively control particle size of the hydrated polyacrylic acid copolymer. Excessive crosslinking of the polymer in the aqueous solution will result in dehydration and precipitation of the polymer. A balance has to be maintained to get optimum viscosity for a particular product. Highly bioadhesive, very low viscosity, (200 to 1000 cps for 3% polymer solution) polymeric dispersions can be produced by interaction of fully hydrated polyacrylic acid polymers lightly crosslinked with polyalkenyl polyethers and hydrophobic organic amine hydrochlorides. Dramatic change in viscosity of the polymeric dispersions makes it possible to formulate bioadhesive products in liquid formulations. A three percent polymer formulation with average viscosity of about 100,000 cps can be formulated as a liquid product by interacting the polymer gel with hydrophobic organic amine hydrochloride like promaxine hydrochloride in therapeutic concentrations. The low viscosity products formed by such interaction tend to have excellent bioadhesive properties and form good films on biological surfaces. Bioadhesive compositions mentioned in this invention also comprise of combination of different polymers of pharmaceutical use to modify physical properties and the release properties of final preparation. Such polymers include Sodium CMC, PVP (K15, K30, K90, K120), Xanthan Gum, Hyaluronic Acid, Alginates, Polylactic Acids, Pectin, Gelatin, Polyethylene Oxide of different molecular weights, Polygeline, (Gantrez type Maleic Acid Copolymers and their Mono, Di and Polyvalent Metal Salts, Natural Gums, (like Acacia, Agaragar, Karaya, Tragacanth, Locust, Guar, Xanthan, Gelan Gum), Cellulose Gums (like Carboxymethylcellulose, Methylcellulose, Hydroxypropyl, Hydroxyethylcellulose, HPMC), Polyacrylic Acid and their Salts, Polyvinyl Alcohol, Polyhydroxyethyl Methicrylate, Polycarbophil etc.

Viscosity becomes a limiting factor for incorporation of the polymer in aqueous systems. Dispersion of the polymer in the hydrophilic hydrating solvent is also a difficult task due to the formation of lumps of poorly hydrated polymers. Adhesive strength and retention time depend on polymer concentration and any effort to increase the polymer concentration in the dispersed system will improve the bioadhesive performance. Acidic polymers in anhydrous form dispersed in anhydrous vehicles tend to be strong irritants due to their low pH and localized dehydration, and therefore, exclude their applications to the sensitive mucous membranes. This is particularly important in the vaginal drug delivery systems as such anhydrous polymers may produce toxic shock syndrome.

The bioadhesive drug delivery system can be formulated in a solid dosage form as a soft gelatin capsule by utilizing unique methods. The polymer and the crosslinking agent are dispersed in a hydrophobic medium and then incorporated into polyethylene glycol of average molecular weight of 200 to 3000. This dispersion is then encapsulated in a soft gelatin shell containing approximately 30 percent glycerin and 30 percent water. Encapsulation of the anhydrous polymer dispersion in aqueous gelatin shell results in quick hydration of the polymer resulting in a hydrated polymer matrix inside the soft gelatin capsule. A variety of drugs can be trapped in soluble and insoluble form inside the soft gelatin capsule in order to get sustained release of active ingredients. This can be demonstrated by incorporation of a water-soluble dye in the matrix and monitoring its release over a period of time. A drug is preferably incorporated in appropriate amount to achieve therapeutic utility in a composition described in this invention.

Drugs that can be delivered but not limited to this invention include:

Analgesics narcotic and non-narcotic (e.g. Morphine, Hydromorphine, Pentazocine, APAP)
Anti-inflammatory drugs steroidal (e.g. Hydrocortisone)
Anti-inflammatory drugs non-steroidal (e.g. Piroxicam, Naproxen, Diclofenac, Ketoprofen, Ibuprofen)
Anti-acne products (e.g. Salicylic Acid, Retinoic Acid, Azelaic Acid)
ACE inhibitors (e.g. Captopril, Lisinopril, Enalapril)
Anorectal agents (e.g. Zinc Acetate, Hydrocortisone, Witch Hazel, Phenylephrine, Cocoa Butter, Shark liver Oil, Pramoxine)
Local anesthetics (e.g. Lidocaine, Pramoxine, Benzocaine)
Topical antibiotics (e.g. Neomycin, Bacitracin)
Steroids (e.g. Testosterone, Estradiol, Progesterone and its conjugates)
Antiparasitics (e.g. Metronidazole, Quinolines)
Antibacterials (e.g.Tetracycline, Erythromycin, Quinolone Antibacterials, Azithromycin
Antiperspirants (e.g. Zinc Salts, Aluminum and Zirconium complexes)
Antiemetics (e.g. Metaclopromide, Ondansetron, Dronabinol, Prochloperazine, Chlorpromazine)
Anticonvulsants (e.g. Phenytoin, Gabapentin, Phenobarbitol, Carbamazepine)
Antispasmodic and anticholinergic (Atropine, Scopolamine)
Artificial tears (e.g. Saline)
Eye drops (Tetrahydrozoline, Naphazoline. Timolol)
Dermatologicals (e.g. Antifungals, Antibiotics, Retinoids, α-Hydroxy Acids, Moisturizers, Keratolytics)
Burn preparations (e.g. Lidocaine, Silver Sulphadiazine)
Antipruritics (e.g. Lidocaine, Pramoxine, Diphenhydramine, Nidocromil, Cromoglycate)
Antifungal (e.g. Miconazole, Econazole, Terconazole)
Antiviral (e.g. Acyclovir, Behenyl Alcohol)
Antidiabetic (e.g. Glipizide, Glyburide)
Antimigraines (Sumatriptan, Ergotamine, Lidocaine And Pramoxine Sustained Release Nasal Spray)
Hair growth stimulants (e.g. Monoxidil, Finasteride, Dexpenthenol, α-Hydroxy Acids)

Histamine blockers (e.g. Diphenhydramine Hydrochloride, Loratadine, Terfenadine)
Hormones (e.g. Insulin, Steroidal Harmones, Calcitonin, Melatonin)
Mouthrinse (e.g. Zinc Salts, Copper Salts, Allantoin, Antibacterials, Fluorides, Flavors, MCT Oils)
Moisturizers (e.g. Water, Glycerin, Petrolatum, Dimethicon, Lactic Acid Salts, α-Hydroxy Acids)
Lip treatment (e.g. Allantoin, Petrolatum, Sunscreens)
Nasal gels (e.g. Vit. B12, Saline, Lidocaine, Glycerin)
Nasal drops/spray (Phenylephrine, Naphazoline, Pyrilamine, Oxymetazoline, Nicotine, Fentenyl)
Sedatives (Barbiturates, Benzodiazepines)
Contraceptives (e.g. Nonoxynol 9)
Wart removers (e.g. Salicylic Acid, Podophylotoxin)
Wet dressings (e.g. Saline Solution)

TEST METHODS

Test 1

In order to determine the bio-adhesive strength and the bioadhesion itself, a simple adhesion test was performed to compare this invention to the marketed product based on Polycarbophil. Ten human volunteers were selected from diverse population and were given instructions to apply 100 mg of the blinded product from a collapsible tube to their lower lips without rubbing. After a period of 5 minutes, the upper and lower lips were pressed together and the force required to separate the lips was evaluated by individuals on one to ten scale. Five measurements were made for in each application and the individual got a chance to evaluate both the formulations on the same day with at least an eight-hour gap between two applications. Water was evaluated as a blank in all the cases. Individuals were also asked to evaluate the physical appearance and the ease of application to the lips. Results of this study indicated that the product formulated with the current invention outperformed 100 percent (ten out of ten subjects) on physical appearance and case of application. With respect to bioadhesion, the product (as described in Example 1) was found to be superior to the current marketed product based on polycarbophil.

Test 2

The adhesion to the skin was evaluated in a moisturizing formulation in comparison with the marketed Polycarbophil moisturizer. Individuals were asked to rub 200 mg on their left arm just below their wrist in the area not exposed to the sun. Ease of application and the adhesive properties were graded by individuals on one to ten scale in a blinded trial (n=10). Panel unanimously concluded that the product formulated with the current invention (Example 1) was superior compared to the marketed moisturizer in terms of appearance, ease of application and adhesive power.

Following are some of the examples that utilize the invention and are provided to illustrate the usefulness of this invention in the pharmaceutical compounding art.

EXAMPLE 1

Controlled Release Vaginal Moisturizer 30.0 grams of the polyacrylic acid-crosslinked allyl sucrose is dispersed in 70.0 grams of squalane containing 0.5 percent vitamin E. This dispersion is added to a mixture of 746.6 grams of water containing 1.5 grams methylparaben and 0.4 gram of propylparaben and 50 grams of glycerin, with vigorous mixing to form a viscous gel. To this gel, 100 grams of water containing 1.0 gram of zinc acetate is added in a controlled manner to get oil in water emulsion. The rate of addition is very important, as fast uncontrolled addition of the zinc salt will result in precipitation of the polymer. The final product has a viscosity of about 85,000 cps. The product formed is found to have excellent bioadhesive power and excellent physical properties. In physical properties and appearance, the consumers preferred this product, two to one, against a marketed bioadhesive gel.

EXAMPLE 2

Controlled Vaginal Moisturizer 60.0 grams of the polyacrylic acid lightly c rosslinked with allyl sucrose having a particle size between 1 to 20 micron is dispersed in 100 grams of a mixture of hydrogenated vegetable oils containing 0.5 gram of vitamin E and 0.5 gram of lecithin. This mixture is added to 685 grams of water containing 1.5 grams of methylparaben, 0.5 gram of propylparaben, and 50 grams of glycerin with vigorous stirring. To the resulting oil in water emulsion, 100 grams of water containing 2.0 grams of zinc acetate is added slowly in a controlled fashion to get the product as an elegant emulsion gel.

EXAMPLE 3

Controlled Release Breath Freshener 40.0 grams of finely divided polyacrylic acid lightly crosslinked with allyl sucrose is dispersed in 70 grams of fractionated medium chain triglycerides containing 2.0 grams of peppermint oil, 0.5 gram of anethol and 1.0 gram of menthol. This dispersion is added to a mixture 581.8 grams of water, 200 grams of glycerin, 1.0 gram of methylparaben, 0.5 gram of propylparaben and 2.0 grams of saccharine with vigorous stirring. To this oil in water emulsion 100 grams of water containing 1.0 gram of zinc acetate and 0.2 gram of copper gluconate is added in a slow controlled fashion to get the cosmetically elegant product to be used as a breath freshening gel emulsion for the treatment of halitosis.

EXAMPLE 4

Bioadhesive Antimicrobial Toothpaste 30.0 grams of finely divided polyacrylic acid lightly crosslinked with allyl sucrose is dispersed in 70 grams of medium chain triglycerides containing 1.0 gram menthol, 1.0 gram of thymol, 0.5 gram of anethol, 0.5 gram of cardamom oil, 1.0 gram of peppermint oil and 10.0 grams acid washed sodium lauryl sulfate. This dispersion is added to a mixture containing 562.5 grams of water, 100 grams of precipitated silica, 10.0 grams colloidal silica, 100 grams of sorbitol, 1.5 grams of benzoic acid, 1.0 gram of methylparaben and 10.0 grams of saccharine. To this dispersion, 100 grams of water containing 1.0 gram of zinc acetate is added in a controlled fashion to get the final product as an opaque good tasting paste with excellent anti bacterial activity. The toothpaste also has bad breath fighting properties. In serial dilution test this product met the test criteria described in the USP for antibacterials.

EXAMPLE 5

Bioadhesive Nasal Gel Moisturizer 30.0 grams of polyacrylic acid lightly cross-linked with allyl sucrose is dispersed in 70 grams of light mineral oil, USP. This dispersion is added to a mixture of 775.3 grams of water containing 2.0 grams of sodium chloride, 20.0 grams of glycerin, 0.8 gram of methylparaben, 0.4 gram of propylparaben and 0.5 gram of phenoxyethanol with vigorous stirring. To the resulting gel emulsion, 100 grams of water containing 1.0 gram of zinc acetate is added in a controlled manner. The resulting product has long lasting moisturizing ability with anti-irritant properties.

EXAMPLE 6

Bioadhesive Unit Dose Sort Gelatin Capsule 10 grams of polyacrylic acid lightly cross linked with allyl sucrose is dispersed in mixture of 80.85 grams of PEG 600, 3.0 grams of peppermint oil, 0.1 gram of zinc acetate, 1.0 gram of anethol, 0.05 gram of copper gluconate and 5.0 grams of medium chain triglycerides to get a uniform dispersion. This suspension is encapsulated with gelatin, glycerin and water mixture to get soft gelatin capsules of average weight 1.0 gram with a strong bioadhesive gel entrapped inside the capsule. Fill volume of the gel is approximately 0.65 gram. The gel formation is based on the fast hydration of the polymer due to the diffusion of water from the gelatin shell into the fill suspension. This type of product has to be fractured into the oral cavity to release bioadhesive composition for halitosis. Sustained release long acting drug composition meant for systemic action can be formulated by incorporating the drug suspension or solution in the soft gelatin capsules.

EXAMPLE 7

Bioadhesive Vaginal Estradiol Cream 30.0 grams of polyacrylic acid lightly crosslinked with allyl sucrose is dispersed in 70.0 grams of squalane containing 0.1 gram of estradiol, 1.5 grams of methylparaben and 1.0 gram of Span 20. This dispersion is added to 700 grams of water containing 30 .0 grams of glycerin with vigorous mixing. 166.4 grams of water containing 1.0 gram of zinc acetate is added at a slow controlled rate with uniform mixing to get a fine polymeric emulsion with bioadhesive properties.

EXAMPLE 8

Bioadhesive Film Forming Burn Treatment 30.0 grams of polyacrylic acid lightly crosslinked with allyl sucrose is dispersed in 70 grams of squalane containing 1.5 grams of methylparaben. This dispersion is added to 700 grams of water containing 10.0 grams of pramoxine hydrochloride with vigorous mixing and homogenizing. To the resulting latex dispersion, 2.0 grams of high viscosity grade HPMC in 25.0 grams of glycerin is added followed by 0.5 gram of zinc acetate in 161.0 grams of water. Resulting lotion is homogenized to get uniform latex dispersion of the polymer in a bioadhesive form.

EXAMPLE 9

Bioadhesive Hemorrhoidal Preparation 70.0 grams of Carbopol 974P, 1.5 grams of methylparaben and 10.0 grams of hydrocortisone are dispersed in 140 grams of squalane containing 0.5 gram of Span 20. 10.0 grams of pramoxine is dissolved in 741 grams of water to get a clear solution. Carbopol dispersion is added to the pramoxine hydrochloride solution with vigorous mixing and homogenization. A Silverson type of homogenizer is used to get good dispersion at 3000 rpm. Addition of the acrylic acid polymer to the pramoxine hydrochloride results in latex type particles with excellent adhesive properties. Particle size of the polymer dispersion will depend on the surfactant concentration and the energy input from the homogenizer. Hydrophobic oil phase seems to be adsorbed at the polymer water interface and to some extent dispersed in the polymer matrix. 2.0 grams of high viscosity HPMC is dispersed in 25 grams of glycerin and added to the gel with vigorous mixing. Polymeric gel product is packaged in laminated collapsible tubes. Gel product is found to be stable at 45° C.

EXAMPLE 10

Bioadhesive Sustained Release Timolol Maleate Eye Drops 15 grams of Carbopol 974P is dispersed in 40 grams of heavy mineral oil USP and is added to 841.5 grams of water containing 2.5 grams of timolol meleate with vigorous stirring. 100 grams of water containing 1.0 gram of zinc acetate is added in a controlled fashion with homogenization to get a particle size distribution size below 5 micron.

EXAMPLE 11

Bioadhesive Long-lasting Nasal Spray 10.0 grams of Carbopol 934P is dispersed in 25 grams of heavy mineral oil USP and to it is added 863.47 grams of water containing 0.5 gram of oxymetazoline hydrochloride and 0.03 gram of phenylmercuric acetate with vigorous stirring. To this dispersion 100 grams of water containing 0.1 gram of zinc acetate is added in a controlled fashion with homogenization to a particle size distribution of about 5 microns.

EXAMPLE 12

Bioadhesive Long-lasting Fluoride Mouth Rinse 30.0 grams of Carbopol 974P is dispersed in 70 grams of PEG 600 containing 1.0 gram of peppermint oil, 1.0 gram of saccharine and 1.0 gram of methylparaben. This dispersion is added to 791 grams of water with vigorous stirring. 1.0 gram of potassium fluoride and 5.0 grams of sodium chloride is dissolved in 100 grams of water and added to the dispersion with vigorous mixing. The resulting solution has excellent bioadhesive and coating properties in the oral cavity.

EXAMPLE 13

Bioadhesive Long-lasting Lip Treatment with Taste-Masked Zinc Ions 30.0 grams of the polyacrylic acid-crosslinked allyl sucrose is dispersed in 70.0 grams of squalane containing 2.5 grams of vitamin E and 10.0 grams of dimethicone 200 cs and 1.0 gram of flavor. This dispersion is added to a mixture of 733.6 grams of water, containing 1.5 grams methylparaben and 0.4 gram of propylparaben, and 50 grams of glycerin, with vigorous mixing to form a viscous gel. To this gel, 100 grams of water containing 1.0 gram of zinc acetate is added in a controlled manner to get oil in water emulsion. The rate of addition is very important, as fast uncontrolled addition of the zinc salt will result in precipitation of the polymer. The final product has a viscosity of about 85,000 cps.

We claim:

1. Sustained release treatment compositions useful for application to biological surfaces comprising skin and mucous membranes of various organs and tissues, said composition containing medicament, water-soluble, and water-swellable polymners, said polymers containing at least 25% by weight of carboxylic acid groups crosslinked with a crosslinking agent selected from the group consisting of polyalkenyl polyether or divinyl benzene, said polymer being present in amounts of 0.05–20 weight percent and being further physically or chemically interacted with a single or a combination of mono, di and polyvalent metallic cations or anions to obtain cross-linked co-polymers of high molecular weight with reduced viscosity and solubility but with enhanced bioadhesive properties, said composition further being comprised of hydrophilic or hydrophobic carrier or a mixture of the same.

2. The treatment composition of claim 1 wherein the cross-linked polymer is first dispersed in a hydrophobic vehicle and then redispersed in hydrophilic vehicle containing medicaments and the crosslinking cation or anion.

3. The composition of claim 2, wherein the hydrophobic vehicle is selected from the group consisting of squalane, mineral oil, petrolatum, silicone oils, mixtures of mono, di and triglycerides and hydrocarbons or combinations thereof.

4. The composition of claim 2, wherein the hydrophilic vehicle is selected from the group consisting of water, polyhydric alcohols, polyethylene and polypropylene glycols of various molecular weights, N-methyl pyrrolidone, NN-dimethyl acetamide and dimethyl isosorbide or combinations thereof.

5. The composition of claim 1, wherein the crosslinked anion or cation treated polymer is dispersed in a hydrophilic medium as a latex in the presence of medicaments and polymer modifing agents.

6. The composition of claim 5, which is formulated as a bioadhesive vaginal gel emulsions.

7. The composition of claim 1, wherein the said composition is selected from the group consisting of dermatological creams, lotions and gels.

8. The composition of claim 1, wherein the said bioadhesive composition is formulated as a sustained or immediate release nasal spray, drop or gel containing medicament.

9. The composition of claim 1, wherein the said composition is formulated as a sustained or immediate release bioadhesive anorectal product in semisolid or suppository form.

10. The composition of claim 5, which is in the form of bioadhesive gels, creams, soft gelatin capsules, and center fill candies for use in the oral cavity.

11. The composition of claim 1, which is in the form of sterile bioadhesive eye drops or inserts, containing a medication.

12. The moisturizing composition of claim 2, wherein the medicament is water.

13. The composition of claim 1, wherein the said composition is encapsulated into soft gelatin capsules as bioadhesive solid dosage forms containing encapsulated medicament.

14. The composition of claim 1, wherein the crosslinked and cation or anion treated polymer is redispersed in presence of a water-soluble polymer in aqueous or non-aqueous medium to obtain desired viscosity for use as a semisolid dosage form containing medicament.

15. The composition of claim 14, wherein the water-soluble polymer used to attain the required viscosity is selected from the group consisting of pharmaceutically or cosmetically useful natural or semisynthetic gum, cellulose gum, or synthetic polymers approved in pharmaceutical and cosmetic formulations and is present in the range from 0.01 to 10 percent w/w.

16. The composition of claim 2, wherein the hydrophobic vehicle is in the range of 0.1 to 30% w/w.

17. The composition of claim 1, wherein the said anions and cations are present as salts of organic or inorganic medicaments.

18. The treatment composition of claim 1, wherein the polymer, in addition to the said cationic or anionic treatment as described in claim 1, is interacted simultaneously or later with one or more of the following in order to modify its properties, and wherein the set of interactions described are, in no particular order:

a). mono or polyamino functional polymers;

b). hydrochloride, bromide, sulfate, phosphate or any other inorganic salts of organic amino compounds;

c). cationic surfactant or cationic polymer.

* * * * *